United States Patent [19]
Crystal et al.

[11] Patent Number: 6,165,754
[45] Date of Patent: Dec. 26, 2000

[54] METHOD OF EXPRESSING AN EXOGENOUS NUCLEIC ACID

[75] Inventors: Ronald G. Crystal, Potomac, Md.; Xiaohuai Zhou; Neil R. Hackett, both of New York, N.Y.; Todd K. Rosengart, Highland Park, Ill.

[73] Assignee: Cornell Research Foundation, Inc., Ithaca, N.Y.

[21] Appl. No.: 09/328,020

[22] Filed: Jun. 8, 1999

[51] Int. Cl.⁷ .......................... C12P 21/00; C12N 15/63; C12N 15/85; A61K 48/00; C07H 21/04
[52] U.S. Cl. ..................... 435/69.1; 435/320.1; 435/455; 514/44; 536/23.1; 536/24.1
[58] Field of Search ................................ 435/69.1, 320.1, 435/455; 514/44; 536/23.1, 24.1

[56] References Cited

U.S. PATENT DOCUMENTS

| | | |
|---|---|---|
| 4,797,368 | 1/1989 | Carter et al. . |
| 5,139,941 | 8/1992 | Muzyczka et al. . |
| 5,252,479 | 10/1993 | Srivastava . |
| 5,834,441 | 11/1998 | Philip et al. . |
| 5,843,742 | 12/1998 | Natsoulis et al. . |
| 5,858,351 | 1/1999 | Podsakoff et al. . |
| 5,861,171 | 1/1999 | Philip et al. . |
| 5,861,314 | 1/1999 | Philip et al. . |
| 5,869,305 | 2/1999 | Samulski et al. . |

FOREIGN PATENT DOCUMENTS

| | | |
|---|---|---|
| WO 95/07995 | 3/1995 | WIPO . |
| WO 98/46273 | 10/1998 | WIPO . |
| WO 99/18227 | 4/1999 | WIPO . |
| WO 99/20773 | 4/1999 | WIPO . |

OTHER PUBLICATIONS

Afione et al., *J. Virol.*, 70, 3235–3241 (1996).
Bartlett et al., *Cell Transplantation*, 5, 411–419 (1996).
Baudard et al., *Human Gene Therapy*, 7, 1309–1322 (1996).
Brigham et al., *CRISP Data Base National Institutes of Health*, Indentification No. 5R01HL45151–08 (1998).
Brinster et al., *Nature*, 296, 39–42 (1982).
Boshart et al., *Cell*, 41, 521–530 (1985).
Cech et al., *Annual Rev. Biochem.*, 55, 599–629 (1986).
During et al., *Soc. Neurosci. Abst.*, 22, 23 (1996).
Fan et al., Gene Therapy, 5, 1434–1440 (1998).
Flotte et al., *J. Biol. Chem.*, 268, 3781–3790 (1993).
Flotte et al., *PNAS USA*, 90, 10613–10617 (1993).
Fu et al., *Nature Biotechnology*, 16, 253–257 (1998).
Hampel et al., *Nucleic Acids Research*, 18, 299–304 (1990).
Huang et al., *CRISP Data Base National Institutes of Health*, Identification No. 1R01DK54225–01 (1999).
Kaplitt et al., *Nature Genetics*, 8, 148–154 (1994).
Kessler et al., *PNAS USA*, 93, 14082–14087 (1996).
Kozak, *J. Molec. Biol.*, 196, 947–950 (1987).
Lebkowski et al., *Blood*, 84 (10 Suppl. 1), 430A (1994).
Lebkowski et al., *Current Top. Microbiol. Immunol.*, 218, 51–59 (1996).
Lo et al., *Human Gene Therapy*, 10, 201–213 (1999).
McLaughlin et al., *J. Virol*, 62, 1963–1973 (1988).
McKnight et al., *Science*, 217, 316–324 (1982).
Mühlhauser et al., *J. Cell Biochem.*, 18A, DZ315 (1994).
Myers et al., *Science*, 229, 242–247 (1985).
Philip et al., *Mol. Cell. Biol.*, 14, 2411–2418 (1994).
Samulski et al., *PNAS USA*, 79, 2077–2081 (1982).
Smith, *Annu. Rev. Microbiol.*, 49, 807–835 (1995).
Wagner et al., *PNAS USA.*, 78, 1441–1445 (1981).
Wu et al., *Gene Therapy*, 3, 246–253 (1996).
Xiao et al., *Experimental Neurology*, 114, 113–124 (1997).
Xiao et al., *J. Virol.*, 70, 8098–8108 (1996).
Xiao et al., *J. Virol.*, 71, 941–948 (1997).
Zolotukhin et al., *J. Virol.*, 70, 4646–4654 (1996).
Orkin et al. Report and recommnendations of the panel to assess teh NIH investment in research on gene therapy, Dec. 1995.
Marshall E Gene therapy's growing pains. Science vol. 269:1050–1055, Aug. 1995.
Verma et al. Gene therapy—promises, problems and prospects. Nature vol. 389:239–242, Sep. 1997.
Anderson WF Human gene therapy. Nature vol. 392:25–30, Apr. 1998.

*Primary Examiner*—Robert A. Schwartzman
*Assistant Examiner*—William Sandals
*Attorney, Agent, or Firm*—Leydig, Voit & Mayer, Ltd.

[57] ABSTRACT

The present invention provides a method of expressing an exogenous nucleic acid in a mammal. The method comprises non-systemically administering to a non-neuronal tissue of said mammal an exogenous nucleic acid operatively linked to a promoter. The exogenous nucleic acid is proximal to at least one native parvoviral inverted terminal repeat and does not require encapsidation. The expression of the exogenous nucleic acid in the tissue is not substantially diminished at 28 days after administration of the exogenous nucleic acid.

44 Claims, 3 Drawing Sheets

METHOD OF EXPRESSING AN EXOGENOUS NUCLEIC ACID

TECHNICAL FIELD OF THE INVENTION

The present invention relates to a method of effecting prolonged expression of an exogenous nucleic acid in a mammal.

BACKGROUND OF THE INVENTION

The ability to introduce nucleic acids into cells and tissues has opened the door to new areas of bioscience research and therapy. A great deal of research has focused on viral and non-viral vectors to overcome the technical hurdles associated with gene delivery. Viral vectors commonly used to deliver exogenous genetic material to host cells include retrovirus, adenovirus and adeno-associated virus.

Retroviruses are enveloped viruses that contain a single-stranded RNA genome. The viral genome is small and uncomplicated, thereby facilitating manipulation and insertion of foreign genes. However, most retroviruses are able to integrate only into the genome of actively replicating target cells. Retroviral vectors are inefficient as far as cell transduction and are limited as to the size of genetic material that can be incorporated (Smith, Annu. Rev. Microbiol., 49, 807–835 (1995)).

Adenovirus is a non-enveloped virus containing linear double-stranded DNA and is associated with mild disease in humans. Adenovirus has the ability to infect a great number of cell types and can infect both dividing and non-dividing cells. However, adenovirus does not incorporate genetic material into the genome of the target cell, instead residing in episomal form. Adenoviral infection is also associated with the formation of an immune response. Therefore, adenovirus infection results in only transient expression of proteins.

Adeno-associated virus (AAV) is a parvovirus, which is dependent on co-infection with another virus for efficient infection of host cells. AAV is a single-stranded DNA virus, which is not associated with any human disease. The recombinant form of the virus (rAAV), which is used most often in in vivo research and clinical trials, has 96% of the viral genome deleted. rAAV is, therefore, incapable of producing the proteins required for replication and encapsidation. As such, rAAV requires both wild-type adenovirus and wild-type AAV or, in the alternative, recombinant plasmids comprising the required complementing genetic material to produce progeny. The use of recombinant AAV has an obvious safety advantage in that the probability of generating wild-type virus is low. Although administration of AAV may induce the production of anti-capsid antibodies, the deletion of the viral genome from rAAV lessens the immune response associated with viral infection, while increasing the amount of exogenous genetic material that can be inserted.

AAV offers prolonged transduction and expression. It has been suggested that this advantage of AAV may stem from the virus's reported ability to integrate into the host cell genome, although it has been demonstrated that AAV does not always so integrate. Despite the potential for prolonged expression, there are many limitations associated with AAV which hinder its use as a gene transfer vector. For example, while AAV can be produced in high titers, the vector is difficult to generate, due to lack of packaging cells and the need for helper virus. The size of genetic material to be introduced into AAV is limited to approximately 4.7 kb, which precludes many desirable therapeutic genes. In addition, the single-stranded AAV genome requires DNA synthesis to double-stranded DNA for a transgene to be expressed. This requirement has been thought to hinder transduction in non-dividing cells or cells with limited DNA synthesis. There also are conflicting reports regarding the ability of rAAV to integrate into target cells, particularly cells in vivo, to obtain long-term expression. (Xiao et al., Experimental Neurology, 114, 113–124 (1997)).

Viral-based methods of gene delivery often do not efficiently infect a broad range of cells or do not direct stable long-term transduction. In either case, repeated administration or large dosages are required to effect substantial, prolonged expression of genetic material. In addition, administration of virus induces an immune response that prevents effective repeated administration of the vectors. While it is possible to administer viral vectors displaying altered antigenic determinants or vary the types of vectors to elude the immune system, preparation and administration of the modified vectors places a significant burden on the researcher or physician.

Non-viral delivery methods, i.e., plasmids and liposome-DNA complexes, do not elicit the immune response associated with some viral vectors, thereby permitting repeated administration of large quantities of vector. However, the efficiency of non-viral mediated transduction is quite low. In situations where non-viral vectors transduce a significant number of cells, gene expression is not stable and diminishes quickly over time.

While introduction of genetic material into cells and tissues has been achieved, there has been little success in achieving prolonged and substantial expression. Therefore, there exists a need for a method of obtaining prolonged, substantially undiminished expression of exogenous nucleic acids in vivo. The present invention provides such a method. This and other objects and advantages of the present invention, as well as additional inventive features, will be apparent from the description of the invention provided herein.

BRIEF SUMMARY OF THE INVENTION

The present invention provides a method of expressing an exogenous nucleic acid in a mammal. The method comprises non-systemically administering to a non-neuronal tissue in the mammal an exogenous nucleic acid operatively linked to a promoter. The exogenous nucleic acid is proximal to at least one native parvoviral inverted terminal repeat and does not require encapsidation. The expression of the exogenous nucleic acid in the tissue is not substantially diminished at 28 days after administration of the exogenous nucleic acid.

The invention may best be understood with reference to the accompanying drawings and in the following detailed description of the preferred embodiments.

DESCRIPTION OF THE PREFERRED EMBODIMENTS

Figure 1B:
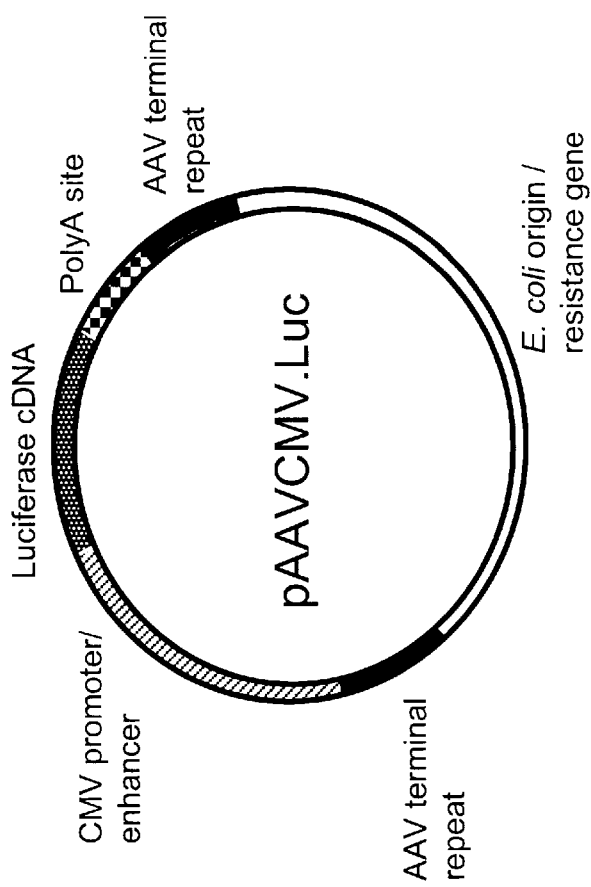
FIGS. 1A and 1B are schematic representations of the pCMV.Luc and pAAVCMV.Luc plasmids, respectively.

It has been recognized that plasmids derived from the AAV genome provide higher levels of gene expression in vitro than plasmids not derived from AAV. However, gene expression in vivo from the AAV virus has been reported to be far superior to the gene expression by both plasmids derived from AAV and plasmids not derived from AAV. Therefore, it was previously believed that the AAV virus is required to obtain high levels of persistent expression in vivo. The present invention is predicated, at least in part, on the discovery that the inverted terminal repeats (ITR) of parvovirus, in particular adeno-associated virus (AAV), are responsible for the high-level persistent nucleic acid expression associated with AAV, not the virus itself.

Accordingly, the present invention provides a method of expressing an exogenous nucleic acid in a mammal that exploits the ability of native parvovirus ITRs to direct not only prolonged expression, but prolonged and substantial expression of exogenous nucleic acids in vivo. The method comprises non-systemically administering to a non-neuronal tissue of a mammal an exogenous nucleic acid operatively linked to a promoter. The exogenous nucleic acid is proximal to at least one native parvoviral ITR and does not require encapsidation. When the plasmid of the present inventive method comprises two ITRs, the exogenous nucleic acid is desirably flanked by the ITRs. While the ITRs can comprise a 5' and a 3' ITR, two 5' ITRs, or two 3' ITRs, preferably the exogenous nucleic acid comprises a 5' and a 3' ITR.

Any suitable parvovirus ITR can be used in the context of the present inventive method. For example, the parvovirus can be an avian parvovirus. Preferably, the parvovirus is a mammalian parvovirus, more preferably, a human parvovirus, such as, for example, a dependovirus and an autonomous parvovirus. Suitable ITRs for use in the present inventive method also include, for example, those native to minute virus of mice, bovine parvovirus, and equine parvovirus. Most preferably, the ITRs are native to AAV.

By administering an exogenous nucleic acid proximal to at least one AAV ITR, such as an exogenous nucleic acid incorporated into a plasmid, the present inventive method bypasses the need to encapsidate and harvest virus as required for recombinant AAV, thereby greatly improving the efficiency of vector preparation and the safety of gene delivery. In addition, the present inventive method introduces exogenous DNA into a target cell or tissue in double-stranded form, unlike rAAV that requires DNA replication to express successfully an erogenous nucleic acid. As such, the present inventive method can effectively transfect non-dividing cells. The present inventive method also allows larger nucleic acids to be introduced into target tissues than can be packaged by retrovirus or AAV.

The present inventive method also offers advantages over the use of adenoviral vectors. While expression of nucleic acids by adenovirus is substantial, it is transient. The present inventive method provides a similar level of expression of an exogenous nucleic acid as adenovirus (see, for example, FIG. 3), but prolonged and substantially undiminished for a longer period of time. In addition, the preparation of an exogenous nucleic acid for use in the present inventive method is easier and less expensive than the preparation of an adenoviral vector incorporating the exogenous nucleic acid.

The levels of nucleic acid expression using the present inventive method have been extraordinary. As illustrated in Example 2 herein, the level of expression is comparable to or exceeds that of expression directed by AAV or adenovirus. The present inventive method provides prolonged, substantially undiminished expression of an exogenous nucleic acid. Indeed, expression of an exogenous nucleic acid in a tissue of a mammal in accordance with the present inventive method is not substantially diminished at 28 days after administration of the plasmid.

By "substantially diminished" is meant less than about 50% of the peak level of expression of the exogenous nucleic acid. Preferably, expression of the exogenous nucleic acid at 28 days is at least about 60% of the level of peak expression. More preferably, the level of expression of the exogenous nucleic acid at 28 days is at least about 80% of the level of peak expression. Most preferably, the level of expression of the exogenous nucleic acid at 28 days is at least about 90% of the level of peak expression (e.g., at least substantially the same as the level of peak expression). Desirably, the aforementioned levels of expression of the exogenous nucleic acid as compared to the level of peak expression are applicable at 42 days, 56 days, or even longer, after administration.

The level of expression of an exogenous nucleic acid in vivo can be determined in accordance with methods known in the art. For example, an exogenous nucleic acid proximal to at least one native parvoviral ITR can comprise a luciferase gene. Expression of the luciferase gene is easily quantitated over time using detection methods that determine activity of the luciferase protein. Example 1 is exemplary of a suitable method for determining expression of an exogenous nucleic acid in accordance with the present inventive method.

The exogenous nucleic acid is administered nonsystemically to a non-neuronal tissue, i.e., directly, administered to a non-neuronal tissue of a mammal. The non-neuronal tissue preferably is an organ or a muscle, such as striated, smooth, or cardiac muscle. Nonsystemic administration provides the maximal amount of exogenous nucleic acid to the target tissue, thereby greatly increasing the incidence of DNA uptake. As such, less genetic material is required.

An "exogenous nucleic acid" is a nucleic acid sequence that is not naturally found in the target tissue. Any suitable exogenous nucleic acid can be employed according to the present invention. Preferably, the exogenous nucleic acid does not encode a rep or cap protein.

The exogenous nucleic acid can comprise sense or antisense sequences, including ribozymes, or catalytic RNA species, such as described in the art (Hampel et al., *Nucleic Acids Research*, 18, 299–304 (1990); Cech et al., *Annual Rev. Biochem.*, 55, 599–629 (1986)), as well as engineered sequences, or sequences which are not normally present in vivo. Furthermore, the exogenous nucleic acid can contain lesions including, but not limited to, a missing base or an altered base (e.g., an alkylated base), a cyclobutyl dimer, strand breaks, and crosslinking of nucleic acid strands.

The exogenous nucleic acid can encode any detectable protein (which term includes peptide and polypeptide), such as a secreted protein or a fragment thereof which comprises the sequence required for secretion. Preferably, such a protein acts systemically or upon or in the vicinity of the target tissue. For example, the protein can have the ability to enhance immune cell recruitment, such as, for example, FLT-3 and MIP-3α. Other proteins contemplated by the present inventive method include, but are not limited to, factor IX, apolipoprotein E, erythropoietin, insulin, and growth hormones.

The exogenous nucleic acid preferably encodes a protein that is relevant to the tissue to which it is administered. For instance, the present inventive method can be utilized to deliver the dystrophin gene to muscle tissue as a therapeutic treatment of muscular dystrophy. Similarly, the present inventive method can be used to deliver to the lung an exogenous nucleic acid sequence encoding the cystic fibrosis transmembrane regulator (CFTR) as a therapeutic treatment of cystic fibrosis.

Exogenous nucleic acids suitable for use in the present inventive method also include, but are not limited to, nucleic acids encoding immunological agents. An "immunological agent" is any agent that evokes or aids in the formation of an immune response. For example, an immunological agent is preferably an antibody or an immunologically reactive fragment thereof. An antibody can be a monoclonal or polyclonal antibody, as well as a single- or double-chain antibody. An immunologically reactive fragment can be the light chain of an antibody, the heavy chain of an antibody, Fab, F(ab')2, Fc, Fc', or pFc'. "Immunologically reactive" refers to the ability to affect the immune response in some manner. For example, the Fc portion of an antibody retains its ability to bind to cell-surface receptors to activate various cells of the immune system. In the alternative, an immunological agent can be an antigen. By "antigen" is meant any substance that may be bound by an antibody or a substance that generates an immune response. One of ordinary skill in the art will appreciate that an antigen can be of any size, shape, or origin as long as the antigen is recognized by some aspect of the immune system, i.e., an antibody. Immunological agents, immunoreactive fragments, and antigens can be determined using routine methods known in the art such as, for example, ELISA, Western blot, and immunoblotting. Similarly, an immunological agent can be a cytokine, such as, for example, tumor necrosis factor (TNF), interferon (INF), or any of the interleukins (IL).

The exogenous nucleic acid for use in the present inventive method also can encode an angiogenic factor, such as one of the vascular endothelial growth factor (VEGF) proteins, particularly $VEGF_{121}$, $VEGF_{145}$, $VEGF_{165}$ (Mühlhauser et al., *J. Cell Biochem.*, 18A, DZ315 (1994)), or $VEGF_{189}$, or other angiogenic growth factors. For example, in addition to the VEGF proteins, aFGF, bFGF, and epithelial growth factor are illustrative of other angiogenic proteins suitable for use in the present inventive method. Angiogenic factors include "angiogenic mRNAs" and "angiogenic proteins," by which is meant any mRNA or protein that is capable of mediating blood vessel formation (angiogenesis).

Similarly, the exogenous nucleic acid can encode a "lymphogenic mRNA" or "lymphogenic protein." VEGF-C is a suitable illustration of a lymphogenic protein.

An exogenous nucleic acid also can encode an "antiangiogenic factor," i.e., an "anti-angiogenic RNA," e.g., an anti-sense molecule or a ribozyme, or an "antiangiogenic protein" that inhibits the vascularity of a given tissue, such as, for example, taxol, angiostatin, endostatin, fumagillin, and analogues thereof, as well as others known in the art. One of ordinary skill in the art will appreciate that "inhibition of vascularity," in the context of the present invention, refers to the inhibition of new blood vessel formation, as well as the inhibition of the growth of existing blood vessels.

The exogenous nucleic acid of the present inventive method also can comprise a selectable marker. The presence of a selectable marker aids in isolation of the exogenous nucleic acid and can be used to indicate successful transduction of target cells and tissues. Examples of selectable markers are β-galactosidase, antibiotic resistance genes, alkaline phosphatase, green fluorescent protein, luceriferase, chloramphenicol transferase, and the like which provide signals which are detectable by standard means, such as color change, wavelength absorbance, etc. Preferably, the exogenous nucleic acid comprises an antibiotic resistant gene.

A "promoter" is a DNA sequence that directs the binding of RNA polymerase and thereby promotes RNA synthesis. According to the invention, an exogenous nucleic acid sequence is "operably linked" to a promoter (e.g., when both the nucleic acid sequence and the promoter constitute a therapeutic gene) when the promoter is capable of directing transcription of that nucleic acid sequence. A promoter can be native or non-native to the exogenous nucleic acid to which it is operably linked.

Any promoter (i.e., whether isolated from nature or produced by recombinant DNA or synthetic techniques) can be used in connection with the present invention to provide for exogenous nucleic acid transcription. The promoter preferably is capable of directing transcription in a eukaryotic (desirably mammalian) cell. The functioning of the promoter can be altered by the presence of one or more enhancers and/or silencers present on the vector. "Enhancers" are cis-acting elements of DNA that stimulate or inhibit transcription of adjacent genes. An enhancer that inhibits transcription also is termed a "silencer." Enhancers differ from DNA-binding sites for sequence-specific DNA binding proteins found only in the promoter (which also are termed "promoter elements") in that enhancers can function in either orientation, and over distances of up to several kilobase pairs (kb), even from a position downstream of a transcribed region.

A comparison of promoter sequences that function in eukaryotes has revealed conserved sequence elements. Generally, eukaryotic promoters transcribed by RNA polymerase II are typified by a "TATA box" centered at approximately position −25, which appears to be essential for accurately positioning the start of transcription. The TATA box directs RNA polymerase to begin transcribing approximately 30 base pairs (bp) downstream in mammalian systems. The TATA box functions in conjunction with at least two other upstream sequences located about 40 bp and 110 bp upstream of the start of transcription. Typically, a so-called "CCAAT box" serves as one of the two upstream sequences, and the other often is a GC-rich segment. The CCAAT homology can reside on different strands of the DNA. The upstream promoter element also can be a specialized signal such as one of those which have been described in the art and which appear to characterize a certain subset of genes.

To initiate transcription, the TATA box and the upstream sequences are each recognized by regulatory proteins which bind to these sites, and activate transcription by enabling RNA polymerase II to bind the DNA segment and properly initiate transcription. Whereas base changes outside the TATA box and the upstream sequences have little effect on levels of transcription, base changes in either of these elements substantially lower transcription rates (see, e.g., Myers et al., *Science,* 229, 242–247 (1985); McKnight et al., *Science,* 217, 316–324 (1982)). The position and orientation of these elements relative to one another, and to the start site, are important for the efficient transcription of some, but not all, coding sequences. For instance, some promoters function well in the absence of any TATA box. Similarly, the necessity of these and other sequences for promoters recognized by RNA polymerase I or III, or other RNA polymerases, can differ.

Accordingly, promoter regions can vary in length and sequence and can further encompass one or more DNA binding sites for sequence-specific DNA binding proteins and/or an enhancer or silencer. Enhancers and/or silencers can similarly be present on an exogenous nucleic acid outside of the promoter per se. The present invention preferentially employs a constitutive promoter, in particular the cytomegalovirus (CMV) promoter, for regulating an exogenous nucleic acid sequence of interest. Such promoters, as well as mutations thereof, are known and have been described in the art (see, e.g., Boshart et al., *Cell*, 41, 521–530 (1985)). Other promoters, however, also can be employed, such as the Ad2 or Ad5 major late promoter and tripartite leader, the Rous sarcoma virus (RSV) long terminal repeat, and other constitutive promoters such as have been described in the literature. For instance, the herpes thymidine kinase promoter (Wagner et al., *Proc. Natl. Acad. Sci.*, 78, 144–145 (1981)), the regulatory sequences of the metallothionine gene (Brinster et al., *Nature*, 296, 39–42 (1982)), promoter elements from yeast or other fungi such as the Gal 4 promoter, the alcohol dehydrogenase promoter, the phosphoglycerol kinase promoter, and the alkaline phosphatase promoter, can be employed. Similarly, promoters isolated from the genome of mammalian cells or from viruses that grow in these cells (e.g., adenovirus, SV40, herpes simplex virus, and the like) can be used.

Instead of being a constitutive promoter, the promoter can be a promoter that is up- and/or down-regulated in response to appropriate signals. For instance, an inducible promoter, such as the IL-8 promoter that is responsive to TNF or another cytokine, can be employed. Other examples of suitable inducible promoter systems include, but are not limited to, the metallothionine inducible promoter system, the bacterial lacZYA expression system, the tetracycline expression system, and the T7 polymerase system. Further, promoters that are selectively activated at different developmental stages (e.g., globin genes are differentially transcribed in embryos and adults) can be employed.

In addition, a tissue-specific promoter, i.e., a promoter that is preferentially activated in a given tissue and results in expression of a gene product in the tissue where activated, i.e., a myocyte-specific promoter, can be used. A promoter exemplary of a myocyte-specific promoter is the myosin light-chain 1A promoter.

With respect to promoters, coding sequences, selectable markers, and the like, located on an exogenous nucleic acid according to the present invention, such elements can be present as part of a cassette, either independently or coupled. In the context of the present invention, a "cassette" is a particular base sequence that possesses functions which facilitate subcloning and recovery of nucleic acid sequences (e.g., one or more restriction sites) or expression (e.g., polyadenylation or splice sites) of particular nucleic acid sequences.

Construction of an exogenous nucleic acid operably linked to a promoter and proximal to at least one native parvoviral ITR is well within the skill of the art (see, for example, Sambrook et al., *Molecular Cloning: A Laboratory Manual*, (2d ed. 1989)). With respect to the transfer and expression of exogenous nucleic acids according to the present invention, the ordinary skilled artisan is aware that different genetic signals and processing events control levels of nucleic acids and proteins/peptides in a cell, such as, for instance, transcription, mRNA translation, and post-transcriptional processing. Transcription of DNA into RNA requires a functional promoter, as described below. Preferably, the exogenous nucleic acid also comprises a bacterial origin of replication.

Protein expression is dependent on the level of RNA transcription that is regulated by DNA signals, and the levels of DNA template. Similarly, translation of mRNA requires, at the very least, an AUG initiation codon, which is usually located within 10 to 100 nucleotides of the 5' end of the message. Sequences flanking the AUG initiator codon have been shown to influence its recognition by eukaryotic ribosomes, with conformity to a perfect Kozak consensus sequence resulting in optimal translation (see, e.g., Kozak, *J. Molec. Biol.*, 196, 947–950 (1987)). Also, successful expression of an exogenous nucleic acid in a cell can require post-translational modification of a resultant protein. Thus, production of a recombinant protein can be affected by the efficiency with which DNA (or RNA) is transcribed into mRNA, the efficiency with which mRNA is translated into protein, and the ability of the cell to carry out post-translational modification. These are all factors of which the ordinary skilled artisan is aware and is capable of manipulating using standard means to achieve the desired end result.

Along these lines, to optimize protein production, preferably the exogenous nucleic acid further comprises a polyadenylation site following the coding region of the exogenous nucleic acid. Also, preferably all the proper transcription signals (and translation signals, where appropriate) will be correctly arranged such that the exogenous nucleic acid will be properly expressed in the cells into which it is introduced. If desired, the exogenous nucleic acid also can incorporate splice sites (i.e., splice acceptor and splice donor sites) to facilitate mRNA production. Moreover, if the exogenous nucleic acid being transferred encodes a protein, which is a processed or secreted protein or, for instance, functions in an intracellular organelle, such as a mitochondrion or the endoplasmic reticulum, preferably the exogenous nucleic acid further comprises the appropriate sequences for processing, secretion, intracellular localization, and the like.

The present invention provides a method of transferring an exogenous nucleic acid to a mammal, which comprises administering the exogenous nucleic acid, preferably as part of a composition (e.g., with a physiological carrier, such as a pharmaceutically acceptable carrier), using routes known to those skilled in the art and appropriate for a particular application. One skilled in the art will recognize that, although more than one route can be used for administration, a particular route can provide a more immediate and more effective reaction than another route. Non-systemic delivery can be accomplished by administration comprising parenteral introduction, comprising intramuscular, peritoneal, subcutaneous, intradermal administration, as well as topical administration. An exogenous nucleic acid of the present inventive method also can be delivered by particle bombardment utilizing, for example, a "gene gun," or may be administered via electroporation. These methods of nucleic acid delivery to target cells and tissues are merely exemplary. Any means of non-systemic administration of exogenous nucleic acids in vivo is appropriate for use in the present inventive me-hod.

One of ordinary skill in the art will appreciate that an exogenous nucleic acid, such as an exogenous nucleic acid incorporated into a plasmid, can be administered alone, i.e., naked DNA, typically in a physiological carrier, or can be complexed with compounds, such as liposomes or molecular conjugates, which facilitate uptake of the exogenous nucleic acid by a target cell. Preferably the exogenous nucleic acid is administered as naked DNA. Also preferably, the exogenous DNA is not encapsidated.

The exogenous nucleic acid can be provided in unit dosage form for administration in the context of the present inventive method, wherein each dosage unit, e.g., a solution, contains a predetermined amount of the exogenous nucleic acid, alone or in appropriate combination with other active agents. The term "unit dosage form" as used herein refers to physically discrete units suitable as unitary dosages for human and animal subjects, each unit containing a predetermined quantity of the exogenous nucleic acid of the present invention, alone or in combination with other active agents, calculated in an amount sufficient to produce the desired effect, in association with a physiological carrier (e.g., a pharmaceutically acceptable carrier) where appropriate. The specifications for the unit dosage forms depend on the particular effect to be achieved and the particular pharmacodynamics associated with the exogenous nucleic acid composition in the particular host.

The "effective amount" of the exogenous nucleic acid composition is such as to produce the desired effect in a host that can be monitored using several end-points known to those skilled in the art. Effective gene transfer of an exogenous nucleic acid to a host cell is confirmed by evidence of the transferred nucleic acid or expression of the exogenous nucleic acid within the host (e.g., using the polymerase chain reaction in conjunction with sequencing, Northern or Southern hybridizations, or transcription assays to detect the nucleic acid in host cells, or using immunoblot analysis, antibody-mediated detection, mRNA or protein half-life studies, or particularized assays to detect protein or polypeptide encoded by the transferred nucleic acid, or impacted in level or function due to such transfer). One such particularized assay includes the Western immunoassay for the detection of the protein encoded by the exogenous nucleic acid. These methods described herein are by no means all-inclusive, and further methods to suit the specific application will be apparent to the ordinary skilled artisan.

Furthermore, the preferred amounts of exogenous nucleic acid used according to the inventive method (e.g., per each cell to be contacted), for example, range from about 1 to at least about 150 µg plasmid DNA, although any suitable amount can be utilized either above, i.e., greater than about 150 µg plasmid DNA, or below, i.e., less than about 1 µg plasmid DNA. These preferred amounts provide general guidance of the range to be utilized by the practitioner to optimize the method of the present invention for practice in vivo. The actual dose and administration schedule can vary depending on whether the exogenous nucleic acid is administered in combination with other active agents, or depending on inter-individual differences in pharmacokinetics, drug disposition, and metabolism. Furthermore, the amount of exogenous nucleic acid to be administered will likely vary with the length and stability of the exogenous nucleic acid, as well as the nature of the sequence. The amount of exogenous nucleic acid administered is limited only by possible toxicity to the mammal, which can be determined using routine dose-determining methods known in the art. One skilled in the art can easily make any necessary adjustments in accordance with the exigencies of the particular situation.

Also, for these embodiments, when one or more different exogenous nucleic acids are employed in the method described herein, the transfection of cells can occur in any order or can occur simultaneously. Preferably the transfection will occur simultaneously. In a preferred embodiment, two or more exogenous nucleic acids are mixed together and preincubated prior to administration to a host.

EXAMPLES

The following examples further illustrate the present invention but, of course, should not be construed as in any way limiting its scope.

All experiments described herein were carried out with a minimum of n=3 animals per data point. The data are presented as mean ± standard error of the mean, and comparisons were made using the two-tailed Student's t-test.

Example 1

This example demonstrates the ability of an exogenous nucleic acid proximal to at least one native parvoviral ITR to effect prolonged and substantially undiminished expression.

Figure 1A:
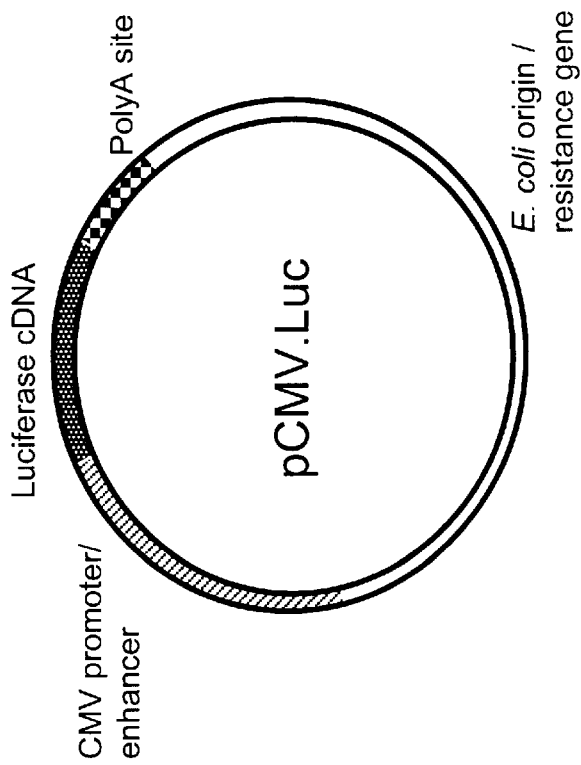

A plasmid that comprises an exogenous nucleic acid, operatively linked to a promoter and flanked by native parvovirus ITRs, was constructed. In particular, pAAVCMV.Luc comprised AAV inverted terminal repeats flanking an expression cassette of the cytomegalovirus (CMV) immediate/early promoter/enhancer and the luciferase reporter gene (Promega, Madison, Wis.). The pAAVCMV-.Luc plasmid was constructed by ligating the XhoI-SalI fragment of an AAV plasmid pTRUF2 (Zolotukhin et al., *J. Virol.*, 70, 4646–4654 (1996)) containing the AAV inverted terminal repeats and the CMV promoter with the XhoI-SalI fragment containing the luciferase cDNA and the SV40 poly(A) stop signal (Promega, Madison, Wis.) from the plasmid pGL2-Basic. A non-AAV plasmid, pCMV.Luc, was constructed by excising the luciferase expression cassette from the pAAVCMV.Luc plasmid with BglII digestion, filling in the ends with Klenow enzyme, and inserting the DNA fragment into PvuII digested pBS vector. pCMV.Luc (FIG. 1A) is identical to pAAVCMV.Luc (FIG. 1B) except that pCMV.Luc does not contain the AAV inverted terminal repeats.

To compare the in vivo expression of a transgene carried out by an AAV plasmid and a non-AAV plasmid, C57BL/6 mice (Taconic Farms, Germantown, N.Y.) were anesthetized with intraperitoneal injection of ketamine and xylazine. Once an adequate plane of anesthesia was established, plasmid DNA (pAAVCMV.Luc versus pCMV.Luc) in a total volume of 50 µl was percutaneously injected into the hind leg tibialis anterior muscles. All studies were carried out using 150 µg plasmid.

Luceriferase activity was quantitated to determine expression of the transgene in the skeletal muscle following administration of plasmid DNA. Muscle tissue was homogenized in four volumes of a buffer containing 53 mM $K_2HPO_4$, 1 mM ethylenediaminetetraacetate, 1 mM dithiothreitol, and 10% glycerol. The suspension was added with the 5× cell culture lysis reagent (Luciferase Assay Kit, Promega), such that the final concentration of the lysis reagent was 1×. The mixture was then vortexed and incubated on ice for 15 min with occasional vortexing, followed by centrifugation in a microfuge at 140,000 rpm for 5 min. Ten µl of the supernatant was then mixed with 100 µl of luciferase assay reagent (Luciferase Assay Kit, Promega) and was immediately measured for luciferase activity in a MONOLIGHT 2010® luminometer (Analytical Luminescence Laboratory, San Diego, Calif.). The data were assessed as relative light units per 8 µl muscle lysate or mg protein with comparable results.

Figure 2:
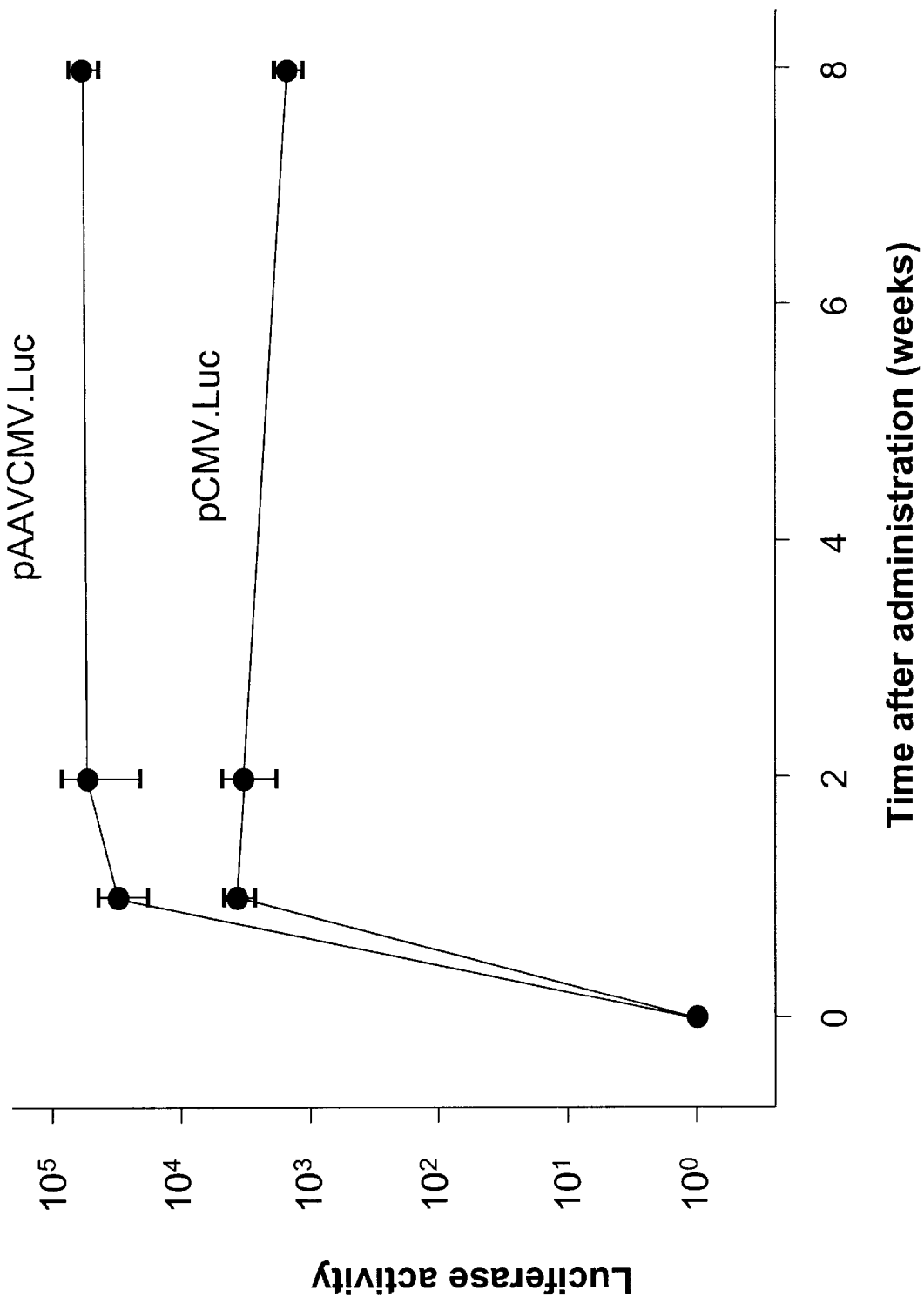
FIG. 2 is a graph of luciferase activity in skeletal muscle, measured as relative light units per 8 µl of muscle lysate, versus time (week) after administration of the pCMV.Luc and pAAVCMV.Luc plasmids.

Administration of the pAAVCMV.Luc plasmid into skeletal muscle of C57Bl/6 mice demonstrated remarkably high expression 1 week after administration, 8.5-fold above that achieved with the comparable non-AAV plasmid pCMV.Luc with an identical expression cassette but without the AAV ITRs flanking the expression cassette (p<0.05; FIG. 2). The most striking observation, however, was at 4 and 8 weeks (i.e., 28 and 56 days), where, as expected, the luciferase expression from the standard pCMV.Luc plasmid was reduced compared to the same plasmid at 1 week. However, the luciferase expression from the pAAVCMV.Luc plasmid had increased above its level of expression at 1 week, such that it was 39-fold greater than that observed with the pCMV.Luc plasmid at the 8 week time point (p<0.01).

These results illustrate the remarkable ability of a plasmid comprising an exogenous nucleic acid flanked by AAV ITRs to direct prolonged, substantially undiminished protein expression for at least 8 weeks after administration.

Example 2

This example illustrates the ability of a plasmid comprising AAV ITRs to direct expression of an exogenous nucleic acid comparable to that of AAV and adenovirus vectors.

An AAV vector (AAVCMV.Luc) was produced by transfecting 293 human embryonic kidney cells (American Type Culture Collection, Manassas, Va.) with a mixture of three plasmids: pAAVCMV.Luc (described in Example 1), pACG2 (comprising the AAV rep and cap genes), and pXX6 (comprising the AdE2A, E4, and VA genes). The resulting vector was purified with a CsCl gradient followed by dialysis in phosphate buffered saline, pH 7.4. The activity of the AAV vector [infectious units (iu)] was determined by a replication center assay (McLaughlin et al., *J. Virol.*, 62, 1963–1973 (1988)).

An adenoviral (Ad) vector (AdCMV.Luc), an E1⁻E3⁻ vector based on the Ad5 genome, contains the identical expression cassette as AAVCMV.Luc. The Ad vectors was produced in 293 cells and purified with CsCl gradients. The activity of the Ad vector [plaque forming units (pfu)] was determined by plaque assay on 293 cells and was demonstrated to be free of replication-competent adenovirus.

Male Sprague Dawley rats (250 to 350 g, Taconic Farms and Charles River Laboratories, Wilmington, Mass.) underwent a left parasternotomy following sedation via intraperitoneal injection of ketamine (80 mg/kg) and xylazine (5 mg/kg). Once an adequate plane of anesthesia was established, animals were intubated with a 20 gauge angiocatheter and mechanically ventilated with a rodent ventilator (Harvard Apparatus, Inc., South Natick, Mass.). The heart was exposed and plasmid DNA (pAAVCMV.Luc as described in Example 1) or viral vectors (AAVCMV.Luc and AdCMV.Luc) were administered to the apical portion of the heart in a total volume of 50 μl. The chest was then closed in layers with an in-dwelling angiocatheter to aspirate any remaining air or fluid from the chest cavity at the termination of the procedure. Once animals were breathing spontaneously, they were disconnected from the ventilator, extubated, and allowed to recover.

Preliminary studies demonstrated no statistical difference in the extent of expression at 2 weeks following administration of 25–100 μg pAAVCMV.Luc. Therefore, all subsequent studies were carried out using 100 μg plasmid DNA. For comparison, the AdLuc vector was administered at $10^8$ pfu in 50 μl and the AACMV.Luc vector at $5 \times 10^7$ IU. AAVCMV.Luc dose-response studies demonstrated that the level of transgene expression reached a plateau at doses above $10^7$ IU. AdCMV.Luc dose-response response studies demonstrated that the transgene expression became saturated at doses above $5 \times 10^7$ pfu. Luceriferase activity was quantitated as set forth in Example 1.

Figure 3:
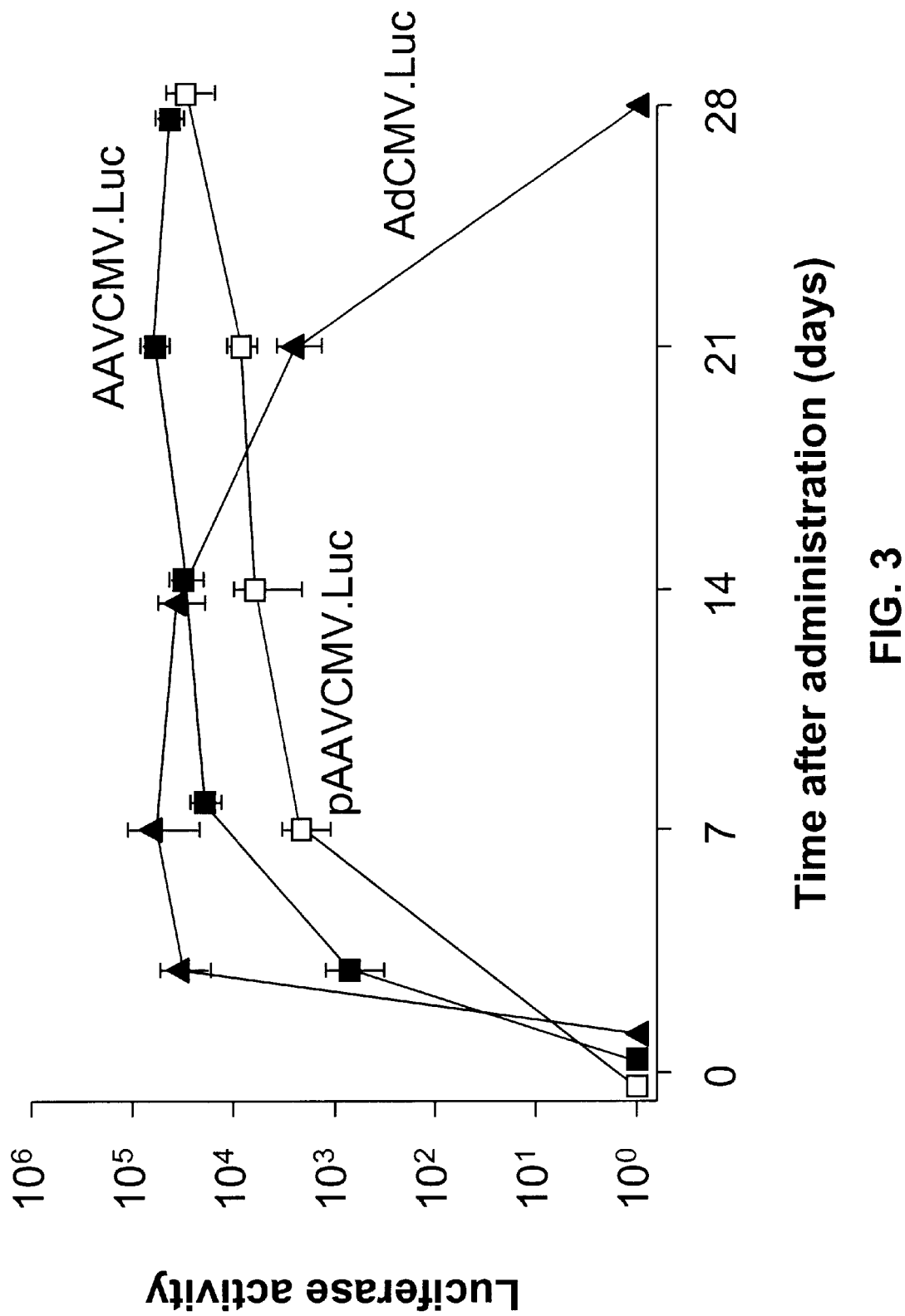
FIG. 3 is a graph of luciferase activity in cardiac muscle, measured as relative light units per 8 µl of muscle lysate, versus time (day) after vector administration of AdCMV.Luc, AAVCMV.Luc, and pAAVCMV.Luc.

Similar to skeletal muscle as illustrated in Example 1, dramatic results were obtained in the myocardium of rats, with the pAAVCMV.Luc plasmid demonstrating levels of transgene expression comparable to that of an AAV vector (AAVCMV.Luc) containing the identical genome (FIG. 3). In this context, the levels of transgene expression achieved with the AAVCMV.Luc vector demonstrated a gradual increase over 3 weeks, where it plateaued, yielding expression of the transgene at 21 days comparable to the peak achieved with the AdCMV.Luc adenovirus vector at 7 days (p>0.9). By 28 days, the AAVCMV.Luc vector remained at the 3 week level, whereas, as expected, the expression directed by the AdCMV.Luc vector had diminished to levels that were undetectable. In contrast to transgene activity over time mediated by the adenoviral vector, the myocardial luciferase levels mediated by the pAAVCMV.Luc plasmid behaved in a fashion similar to that mediated by the AAV virus vector. In this regard, myocardial luciferase activity following administration of the pAAVCMV.Luc plasmid gradually increased over time, with levels 28 days after administration similar to that achieved by the AAVCMV.Luc virus (p>0.4). At the same time, expression mediated by the AdCMV.Luc vector was undetectable.

These results further illustrate the remarkable ability of a plasmid comprising an exogenous nucleic acid flanked by AAV ITRs to direct prolonged, substantially undiminished protein expression for at least 28 days after administration.

All of the references cited herein, including patents, patent applications, and publications, are hereby incorporated in their entireties by reference.

While this invention has been described with an emphasis upon preferred embodiments, it will be obvious to those of ordinary skill in the art that variations of the preferred embodiments may be used and that it is intended that the invention may be practiced otherwise than as specifically described herein. Accordingly, this invention includes all modifications encompassed within the spirit and scope of the invention as defined by the following claims.

What is claimed is:

1. A method of expressing an exogenous nucleic acid in a mammal, wherein said method comprises nonsystemically administering to a non-neuronal tissue of said mammal an exogenous nucleic acid, which is operatively linked to a promoter, flanked by native parvoviral inverted terminal repeats, and does not require encapsidation, wherein expression of said exogenous nucleic acid in said tissue is not substantially diminished at 28 days after administration of said exogenous nucleic acid.

2. The method of claim 1, wherein said exogenous nucleic acid is administered directly into an organ of said mammal.

3. The method of claim 1, wherein said exogenous nucleic acid is administered directly into cardiac muscle.

4. The method of claim 1, wherein said exogenous nucleic acid is administered directly into striated muscle.

5. The method of claim 1, wherein said exogenous nucleic acid is administered directly into smooth muscle.

6. The method of claim 1, wherein said promoter is an inducible promoter.

7. The method of claim 1, wherein said promoter is a tissue-specific promoter.

8. The method of claim 1, wherein said promoter is a cytomegalovirus (CMV) promoter.

9. The method of claim 1, wherein said exogenous nucleic acid further comprises a bacterial origin of replication.

10. The method of claim 1, wherein said exogenous nucleic acid encodes a secreted protein.

11. The method of claim 1, wherein said exogenous nucleic acid is not encapsidated.

12. The method of claim 1, wherein said exogenous nucleic acid does not encode a rep or cap protein.

13. The method of claim 1, wherein said exogenous nucleic acid is administered as naked DNA.

14. The method of claim 13, wherein said exogenous nucleic acid is administered directly into an organ of said mammal.

15. The method of claim 13, wherein said exogenous nucleic acid is administered directly into cardiac muscle.

16. The method of claim 13, wherein said exogenous nucleic acid is administered directly into striated muscle.

17. The method of claim 13, wherein said exogenous nucleic acid is administered directly into smooth muscle.

18. The method of claim 13, wherein said promoter is an inducible promoter.

19. The method of claim 13, wherein said promoter is a tissue-specific promoter.

20. The method of claim 13, wherein said promoter is a CMV promoter.

21. The method of claim 13, wherein said exogenous nucleic acid further comprises a bacterial origin of replication.

22. The method of claim 13, wherein said exogenous nucleic acid encodes a secreted protein.

23. The method of claim 13, wherein said exogenous nucleic acid is not encapsidated.

24. The method of claim 13, wherein said exogenous nucleic acid does not encode a rep or cap protein.

25. The method of claim 13, wherein said exogenous nucleic acid further comprises a selectable marker.

26. The method of claim 25, wherein said selectable marker is an antibiotic resistance gene.

27. The method of claim 13, wherein the level of expression of the exogenous nucleic acid at 28 days is at least about 60% of the level of peak expression.

28. The method of claim 27, wherein the level of expression of the exogenous nucleic acid at 28 days is at least about 80% of the level of peak expression.

29. The method of claim 28, wherein the level of expression of the exogenous nucleic acid at 28 days is at least about 90% of the level of peak expression.

30. The method of claim 13, wherein said exogenous nucleic acid encodes an immunological agent.

31. The method of claim 30, wherein said immunological agent is an antibody or am immunologically reactive fragment thereof.

32. The method of claim 31, wherein said immunologically reactive fragment is the light chain of an antibody.

33. The method of claim 31, wherein said immunologically reactive fragment is the heavy chain of an antibody.

34. The method of claim 31, wherein said immunologically reactive fragment is Fab, F(ab')2, Fc, Fc', or pFc'.

35. The method of claim 1, wherein said exogenous nucleic acid further comprises a selectable marker.

36. The method of claim 35, wherein said selectable marker is an antibiotic resistance gene.

37. The method of claim 1, wherein the level of expression of the exogenous nucleic acid at 28 days is at least about 60% of the level of peak expression.

38. The method of claim 37, wherein the level of expression of the exogenous nucleic acid at 28 days is at least about 80% of the level of peak expression.

39. The method of claim 38, wherein the level of expression of the exogenous nucleic acid at 28 days is at least about 90% of the level of peak expression.

40. The method of claim 1, wherein said exogenous nucleic acid encodes an immunological agent.

41. The method of claim 40, wherein said immunological agent is an antibody or an immunologically reactive fragment thereof.

42. The method of claim 41, wherein said immunologically reactive fragment is the light chain of an antibody.

43. The method of claim 41, wherein said immunologically reactive fragment is the heavy chain of an antibody.

44. The method of claim 41, wherein said Immunologically reactive fragment is Fab, F(ab')2, Fc, Fc', or pFc'.

* * * * *